United States Patent [19]

Miwa

[11] Patent Number: 4,545,250
[45] Date of Patent: Oct. 8, 1985

[54] MEASURING APPARATUS UTILIZING SPECTRUM PROFILE

[75] Inventor: Hirohide Miwa, Kawasaki, Japan

[73] Assignee: Fujitsu Limited, Kawasaki, Japan

[21] Appl. No.: 590,883

[22] Filed: Mar. 19, 1984

[30] Foreign Application Priority Data

Mar. 18, 1983 [JP] Japan .................................. 58-45396

[51] Int. Cl.$^4$ ........................................... G01N 29/00
[52] U.S. Cl. ......................................... 73/602; 73/599
[58] Field of Search ................ 73/602, 599, 606, 607, 73/620; 128/660; 364/508, 576; 367/87, 99

[56] References Cited

U.S. PATENT DOCUMENTS 4,052,889 10/1977 Mucciardi et al. .................... 73/602

*Primary Examiner*—Stephen A. Kreitman
*Attorney, Agent, or Firm*—Staas & Halsey

[57] ABSTRACT

This invention relates to an apparatus for measuring of imaging the characteristic structure of a medium utilizing the power spectrum profile of received signal waves, which are derived from an incident beam pulse of ultrasonic waves or other waves that are incident on the object to be measured and which travel through the object by transmission and reflection. They are affected by various acoustic characteristic structures of the object, and information about the structure can be attained by the procession of the signals received with a transducer. The processing is performed by taking their cepstrum, and filtering the slowly varying cepstra including that of the target Gaussian shaped pulse signal from the fast varying cepstra. The filtered cepstrum is processed further by the inverse transformations to the power spectrum derived from said filtered cepstrum. The influence of line cepstra remaining still in the lower frequency and the frequency dependence of the reflection indices of the structure to the derived power spectrum is eliminated by the distortion indices of said derived power spectrum. Thus the travelled power spectrum is recovered as a virtual spectrum, expected when such influences do not exist. Tissue characteristics are extracted from the recovered spectrum. The distortion indices are represented by various order moments of the derived power spectrum.

14 Claims, 22 Drawing Figures

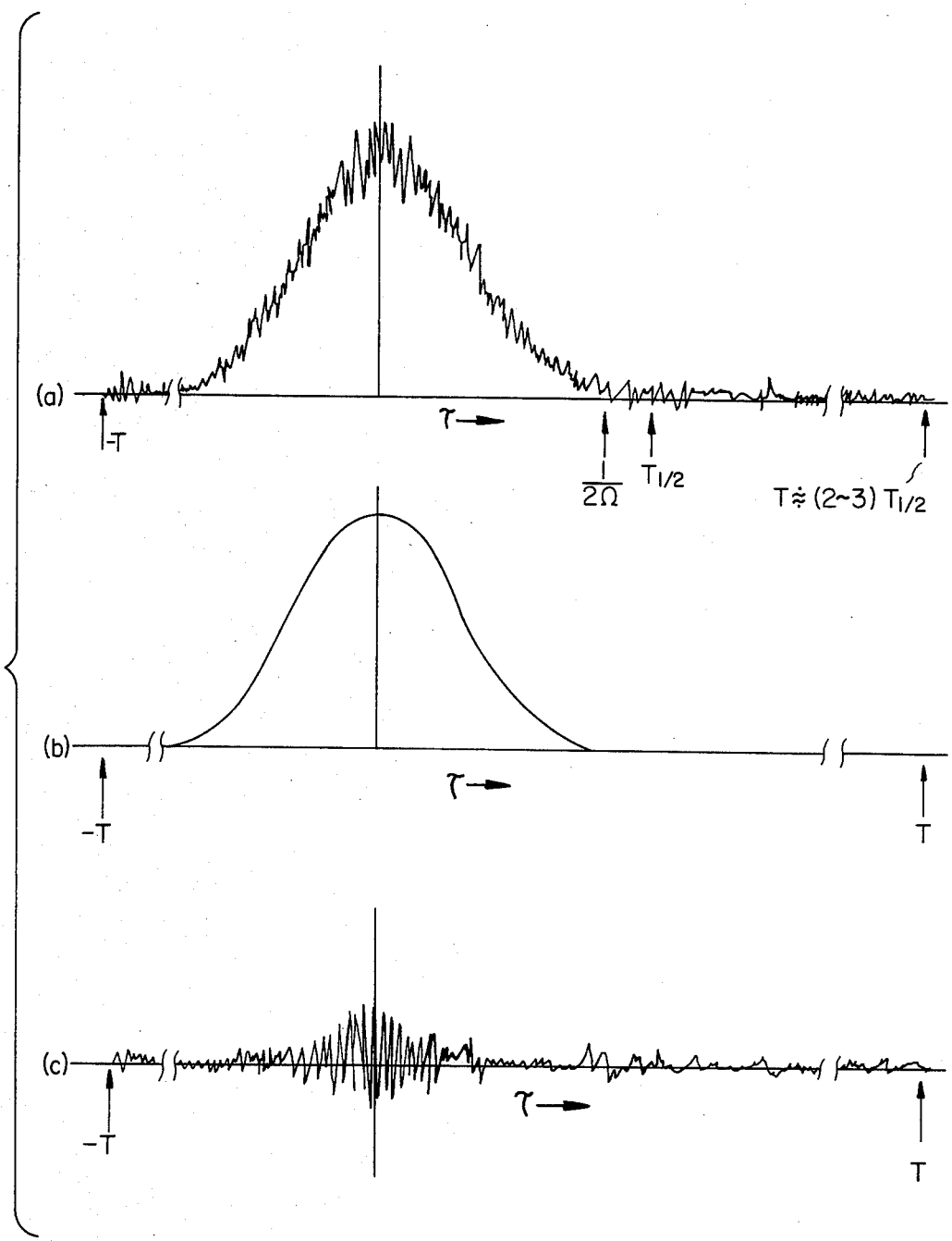

FIG. 9.
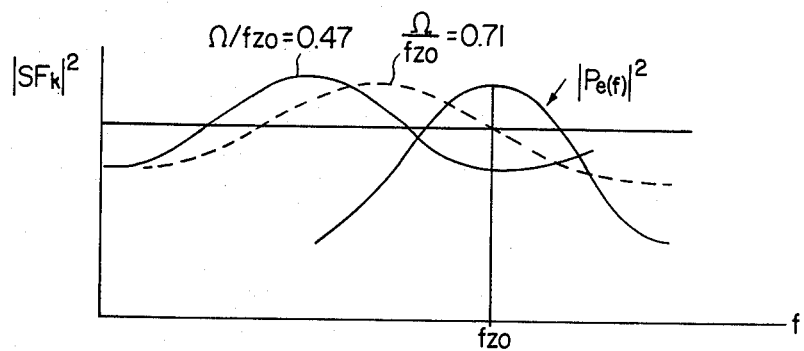
FIG. 10.
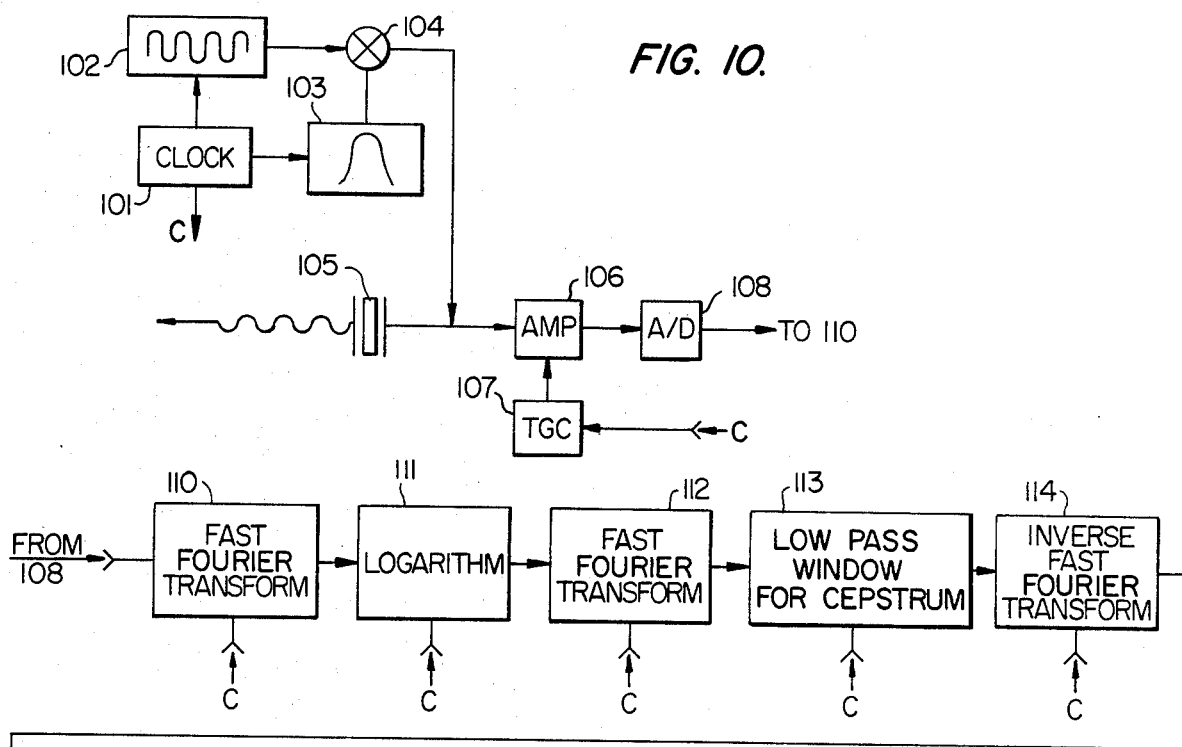
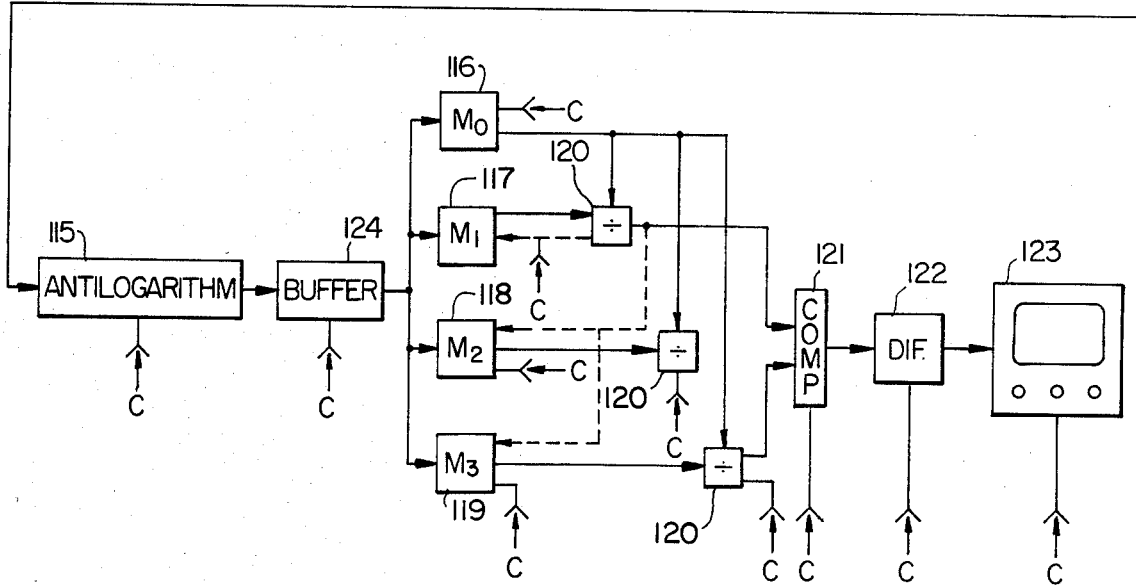

MEASURING APPARATUS UTILIZING SPECTRUM PROFILE

BACKGROUND OF THE INVENTION

This invention relates to a measuring apparatus utilizing the spectrum profile of an incident pulse beam, such as an ultrasonic beam, on the object to be measured. More particularly, it relates to an apparatus having an effective signal processing means to measure and image some characteristics of the object quantitatively by correcting the distorted spectrum profile obtained from the received signal.

Such measuring apparatuses involve radars, sonars, ultrasonic equipment and so on. Hereafter, an ultrasonic device will be described as an example of the present invention, but the invention is applicable to other types of equipment utilizing electromagnetic waves.

The ultrasonic measuring devices are used for various purposes such as medical diagnosis, industrial crack detectors and the like. Generally, an ultrasonic pressure wave beam is generated in a transducer converting electric energy to acoustic energy and is applied to an object to be measured. If the object is completely homogeneous, the beam simply transmits through the object and is subject to attenuation, but, from a practical viewpoint, an object to be measured is heterogeneous and contains various structures of different acoustic characteristics. Accordingly, the beam is reflected at many points inside the object, thus generating multi-reflection. The reflection of the ultrasonic sound in a medium is caused by the difference of acoustic impedance (defined as the product of material density and sound speed) of the adjoining tissues. Hereafter such a boundary will be called a reflecting element. As the applied ultrasonic beam, usually in the form of a pulse, travels through the object, it is affected by the acoustic characteristics of the object such as attenuation, frequency dependency of the attenuation, reflection, diffraction, scattering and the like. As a result, the ultrasonic beam is carrying some acoustic information regarding the internal structure of the object. The signal carried by the transmitted beam or the reflected beam (echo) is received by a receiving transducer and converted into an electric signal which is processed by electronic devices to read the carried information and to display it on a display device such as a cathode ray tube.

In a heterogeneous medium (object) like biological tissue, composed of media of various kinds and structure, the propagating ultrasonic pulse waves have a complicated behavior. A pulse beam is reflected at each of the reflecting elements which are located in the beam path and generates multiple echos. Also, the pulse beam is diffracted or scattered. Thus some of the pulse waves will take the same path and interfere with each other. Moreover, the reflection coefficient is very frequency dependent. These provide serious distortion to the received signal, which make it difficult to quantitatively recover the travelled spectrum of the incident pulse, which reaches the reflecting element and returns back to the detector and the information regarding the object becomes ambiguous. In the case of transmission, some parts of the transmitted beam take different paths due to refractions and diffractions before being finally received by the receiver. This causes pulse overlap and gives quite the same effects as reflection. This is serious problem, and exact recovery of the incident spectrum by eliminating the distortion in the received signal has been desired. Many approaches have been considered for solving this problem.

Hereafter, the term "travelled spectrum" is used to mean the received echo spectrum less the effect of pulse overlap (scallopings) and frequency dependent reflection in the reflection mode, and the transmitted pulse spectrum less the multi-path effect in the transmission mode.

SUMMARY OF THE INVENTION

It is an object of the present invention to provide an apparatus for measuring some of the characteristics of the object, such as attenuation coefficient, heterogeneity, etc., utilizing the spectrum profile of the received signal transmitted through or which perform a round trip in the object to be measured quantitatively.

A further object is to provide the device with a signal processing means for separating the distortion from the spectrum profile of the received signal, such as spectrum scalloping and frequency dependence of the reflection index of the reflecting elements.

Another object of the present invention is to provide a measuring and/or imaging apparatus for the characteristics utilizing the spectrum profile of the received signal with higher spatial and temporal resolution. By contrast, the conventional method of removing the spectrum scallopings is statistical averaging of the spectrum spatially and temporally, with sacrifice of spatial/temporal resolution.

With a conventional signal processing means, such as homomorphic filtering, the received signal is processed to obtain the cepstrum first, and the resulting line-like cepstra corresponding to scalloping in the higher frequency range are liftered out, but still the slowly varying scalloping remains in the lower quefrency region, mixing with the cepstrum corresponding to the travelled pulse (scalloping and quefrency are acoustic technical terms and will be explained later).

Furthermore, reflection at various reflecting elements varies with the wave frequency. The above-mentioned residual slow scalloping and the frequency dependent reflection effect distort the incident profile, which results in erroneous measured results of the characteristics. This problem has not been solved in the prior art.

The processing means according to the present invention is capable of removing the effects due to the residual slowly varying scalloping and to the frequency dependency of the reflecting elements on the travelled wave profile. As a result, the travelled wave spectrum profile can be recovered correctly. Thus, correct characteristics of an object can be measured utilizing the correct spectrum profile. The signal processing apparatus will be disclosed in detail.

BRIEF DESCRIPTION OF THE DRAWINGS

FIGS. 1(a) to 2(c) illustrate distortion caused in two overlapping waves, as follows.

FIGS. 1(a) and (b) respectively illustrate waveforms having the same profile but a time lag $\tau_1$ between them;

FIG. 1(c) illustrates the composite wave of the waves shown in FIGS. (a) and (b);

FIGS. 1(d) and (e) illustrate the power spectra of the waves shown in FIGS. 1(a) and (c), respectively;

FIG. 2(a) illustrates the logarithm of the power spectrum shown in FIG. 1(c);

FIG. 2(b) illustrates the cepstrum corresponding to the power spectrum shown in FIG. 1(e);

FIG. 2(c) illustrates the cepstrum of FIG. 2(b) after being liftered with a lifter;

FIG. 8(a) illustrates a magnitude cepstrum profile of an echo pulse;

FIG. 8(b) illustrates a lowpass filtered and/or liftered cepstrum profile corresponding mainly to the travelled echo pulse having a Gaussian distribution but modified due to $f^n$ power reflection and slow scalloping;

FIG. 8(c) illustrates a profile of the high pass filtered magnitude cepstrum shown in FIG. 8(a);

FIG. 9 illustrates a power spectrum of the low pass liftered echo pulse and scalloping fctors for $\Omega = p.47f_{z0}$ and $\Omega = 0.71f_{z0}$;

FIG. 10 illustrates a block diagram of a measuring apparatus according to the present invention, having a signal processing means, for utilizing a power spectrum profile of an ultrasonic pulse beam, extracting attenuation slope and displaying the tomographic image.

DESCRIPTION OF THE PREFERRED EMBODIMENTS

Figure 1:
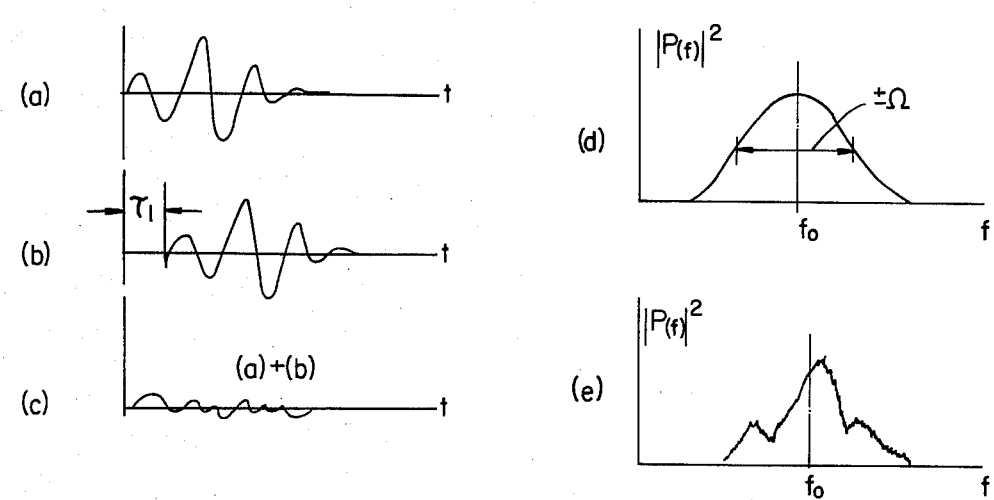

In order to understand the ultrasonic measuring device in principle, a simple interaction between two overlapping waves will be described briefly. A pulse wave as in FIG. 1(a) and a wave having the same waveform and a time delay $\tau_1$ as in FIG. 1(b) are superimposed to form a resultant wave as in FIG. 1(c). The waves of FIGS. 1(a) and (b), naturally, each have the same power spectrum of FIG. 1(d) with a smooth profile but the power spectrum of the composite wave of FIG. 1(c) is an indented curve as in FIG. 1(e), similar to the shape of a cross section of a scallop shell. From this similarity, the indentation of the spectrum of FIG. 1(e) is called a scalloping. In a heterogeneous medium such as a biological tissue, it is unavoidable that transmitted waves and their echos take overlapped propagation paths and interact with each other. This results in scalloping in the power spectrum of the overlapped signal. Accordingly, there arises a difficulty in recovering the travelled wave profile of FIG. 1(d) from the scalloped spectrum FIG. 1(e) and in extracting characteristics regarding the object.

There are two prior art procedures for recovering the travelled spectrum profile. The first one is an averaging method. If plural ultrasonic beams are scanned to cover a finite spatial region inside the object, the echo signals from many locations around the points of interest along each scanning path are combined to provide the averaging ensemble, and the averaged spectrum profile becomes smooth statistically. These methods are basically a statistical averaging method which requires a fairly large space around the point of interest, as the sufficient number ensemble necessary to smooth the scalloping. Such a large space looses spatial resolution. For example, with tissue of the human body, the spatial resolution of this method is usually 30 mm square. In addition, the smoothing effect is often unsatisfactory.

Figure 2:
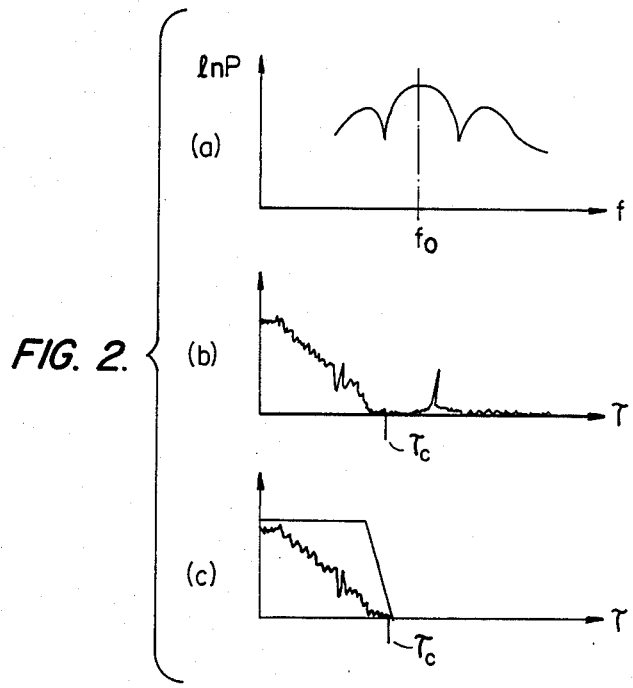

The second method is known as homomorphic filtering utilizing a "cepstrum", which is commonly used in analyzing seismic waves and geological strata investigations. The cepstrum is illustrated in FIG. 2(b), and is obtained by Fourier transformation of the logarithm of the power spectrum $\ln |P(f)|^2$. The abscissa is time lag or "quefrency" ($\tau$ axis), with units of time as in FIG. 2(a) to (c). The time lag $\tau_1$ between two identical waveforms result in line cepstra as shown in FIG. 2(b). In a geological stratum investigation, a layer location is analyzed using this lag time. It is also possible to recover the travelled pulse spectrum by cutting off the line cepstra in the higher quefrency range above a cutoff quefrency $\tau_c$. This cutting off is perfomed by applying a low pass window (this windowing is called "liftering" in the case of handling the cepstrum), which passes the cepstrum corresponding to the power spectrum of FIG. 1(d), but rejects the cepstrum corresponding to the scalloping. Finally a cepstrum as in FIG. 2(c) is obtained and the original spectrum as in FIG. 1(d) can be derived by performing the inverse transformation consecutively.

With the second method mentioned above, information regarding the acoustic characteristics of the object is obtained by analyzing the recovered (i.e. received) power spectrum. This method is effective when the line spectra of the cepstrum corresponding to the scalloping exist apart from that corresponding to the incident wave, and can be separated clearly and easily, like in seismic wave analysis. This operation is what is involved in the homomorphic filtering method. The measured results of the attenuation coefficient of ultrasonic sound waves utilizing the above-mentioned method are reported, for example, in:

Ultrasonic Imaging 4. p. 234–266, 1982, by C. R. Crawford, A. C. Kak, Multipath Artifact Correction in Ultrasonic Transmission Tomography; and NBS special Publ. 525, PP125–134, 1979, by J. Fraser, G. S. King, J. Birnholz, Ultrasonic Tissue Characterization 2.

However, when there are various closely spaced intervals in micro-structures like tissues of the human body, they result in various time lags $\tau$, some of which are shorter than the cutoff quefrency $\tau_c$. Accordingly, the separation of the line cepstra corresponding to the scalloping is not practical, and a log of them still remain together in the quefrency ranges corresponding to the travelled pulse even after the liftering. The power spectrum is derived by inverse-Fourier and inverse-logarithm transformations of the liftered cepstrum. At this stage, the remaining line cepstra corresponding to scalloping in the lower quefrency range, below $\tau_c$, provide the derived power spectrum with a serious distortion or deformation and prevent obtaining exact characteristics of the object.

Especially in the human body, the object to be measured includes various sizes of tissue from a cell of around 10 $\mu$m to blood vessels of few mm in diameter.

The distance $\delta$ between each reflecting element causes a time lag $\tau$ given by the formula $\tau = 2\delta/C$, where C is the sound velocity in the medium. Accordingly, the cepstrum of human body tissue contains many line cepstra in the range of lower quefrency near $\tau = 0$. Generally $\tau$ is regarded to have an almost continuous Gaussian or exponential probability density distribution, and is an even function with respect to $\tau = 0$ axis. This causes a serious distortion in the finally recovered power spectrum which is thus inadequate for performing medical diagnosis.

In addition there is another undesirable effect, namely the frequency dependent refelection index of the microstructure inside the object. This dependence affects the profile of the incident spectrum with additional distortion.

Figure 3:
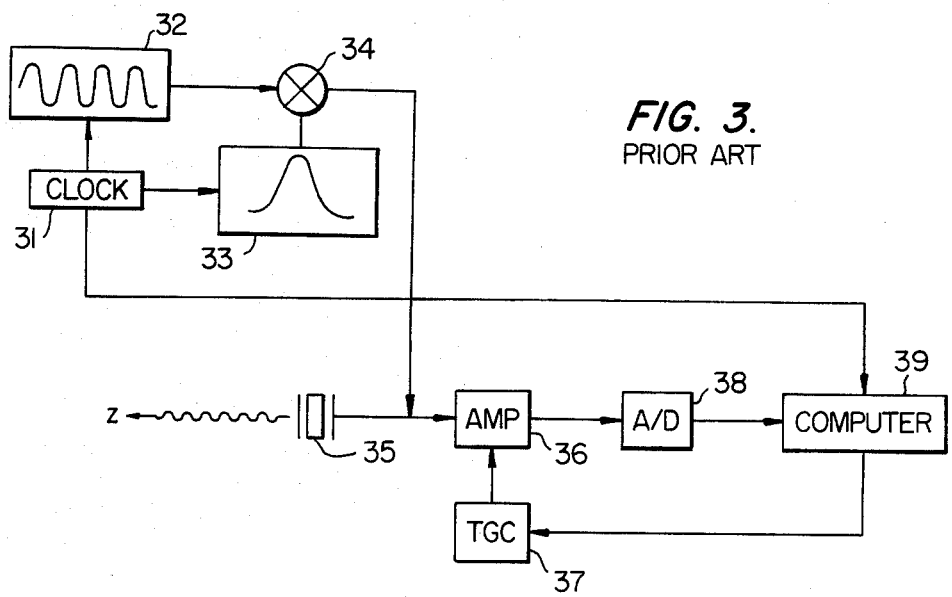
FIG. 3 illustrates a circuit for generating a Gaussian shaped transmitting ultrasonic pulse wave.
Figure 4:
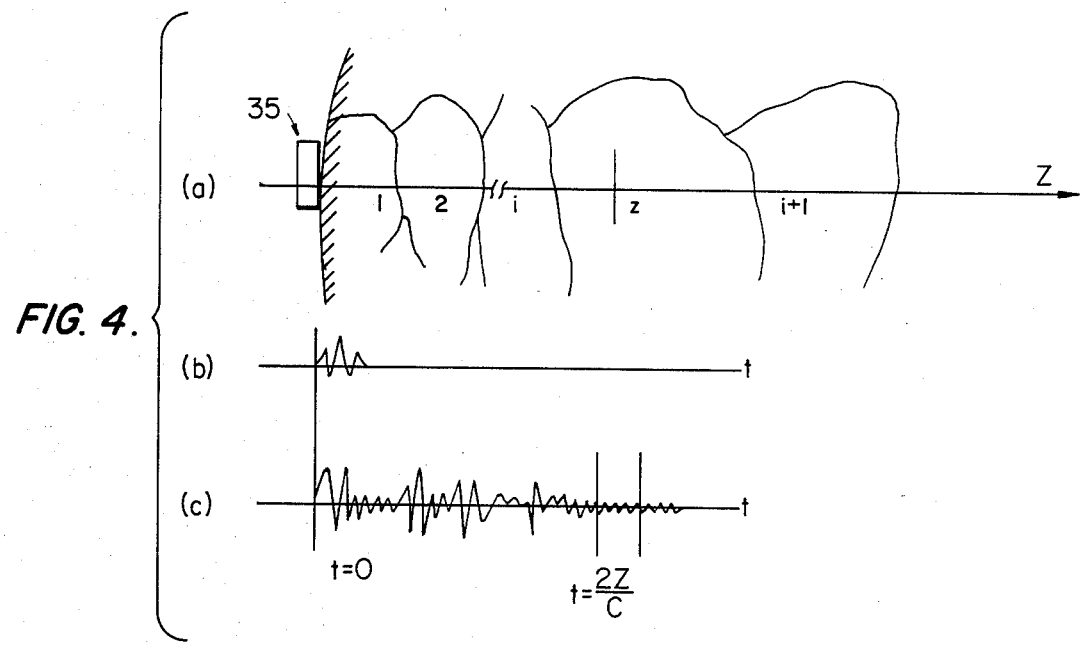
FIG. 4(a) illustrates schematically the tissues of a human body to be measured with an ultrasonic pulse wave in reflection.
FIG. 4(b) illustrates a wave form of a transmitted ultrasonic pulse.
FIG. 4(c) illustrates a wave form of a received signal wave reflected at reflecting elements inside the object.

As a preferred embodiment of the present invention, an ultrasonic device for medical diagnosis is indicated in FIG. 3. A piezo-electric transducer transmits an originally incident ultrasonic pulse into a human body from the skin surface, and receives reflected signals (echos) returning to the transducer. The received echos are converted into electrical signals and processed with electrical circuits or computers. The echo signals are analyzed and the distribution of the attenuation slope is obtained as a function of z along the travel path (scan line) along the z axis, directed into the inside of the body. Finally, the information is processed and the attenuation slope distribution is displayed on a display device such as a cathode ray tube.

FIG. 3 illustrates a circuit for generating a transmitting pulse of a Gaussian shape. The pulse has a center frequency $f_0$ and a Gaussian envelope. A continuous sine wave of a frequency $f_0$ is generated with an oscillator 32, which is controlled by a clock generator 31 involving a frequency divider, which steps down the clock frequency by $1/n$ to $f_0$. A Gaussian signal generator 33 has a memory storing an A/D converted Gaussian envelope signal as a function of time, which is read out in sequence under the control of the clock signal. This output is transformed by a D/A converter included in the signal generator 33 to provide a Gaussian envelope signal, which is multiplied with the output of the oscillator 32 using the multiplier 34. Thus a transmitting pulse having an exact Gaussian envelope as shown in FIG. 1(d) is obtained and this results in an exact Gaussian spectrum.

A piezoelectric transducer 35 is a device capable of converting electrical energy to acoustic energy and vice versa, and various materials of high piezoelectric efficiency such as PZT have been developed for the transducer material. In the example of FIG. 3, one transducer 35 is used for both transmitting a pulse as in FIG. 1(a) and receiving the reflected echoes.

Non-linearity of the transducer 35, if any, can be corrected by a pre-determined compensating circuit in the signal generator 33 in order to obtain a correct Gaussian wave shape of the ultrasonic beam. Non-linearity of the receiving transducer can also be corrected electrically with an amplifier 36, and A/D converter 38 of a computer 39. A time gain controller (TGC) 37 controls the output gain of the amplifier 36 according to a predetermined time program. The microcomputer 39 stores the A/D converted received echo signal in digital form and performs necessary signal processing. These individual devices are conventional and available in the commercial market. The computing process is conducted by the aid of software, but if higher processing speed is important, it is desirable to put all or a part of the program stored in the software into hardware so as to be processed on a real time basis. This case will be described in another embodiment below.

Before describing the function of the apparatus, to provide better understanding, the physical principles of ultrasonic wave propagation in a body will be described briefly. The pulse length of a Gaussian envelope ultrasonic pressure wave with a center frequency $f_0$ and having a half-maximum-width in time of $T_{\frac{1}{2}}$ can be considered to be approximately from two to three times $T_{\frac{1}{2}}$. The power spectrum of the Gaussian waveform pulse also has Gaussian profile with a central frequency $f_0$ and a half-maximum-width $\Omega$, namely a frequency bandwidth $\Omega$, expressed as $$\Omega = 0.625/T_{\frac{1}{2}} \tag{1}$$

An ultrasonic pulse incident on the surface of a human body propagates internally along a path (z-axis), which is usually a straight path. It is subject to a frequency dependent attenuation loss (sum of absorption, scattering, reflection, back scattering, diffraction and refraction) and a frequency independent stepwise specular transmission loss (caused by mirror-like reflection and refraction at a boundary between two organs). The attenuation coefficient is expressed by the following formula:

$$\alpha(z) = \beta(z)f \tag{2}$$

where $\beta(z)$ is called the attenuation slope, and f denotes the frequency of the sound waves.

It is assumed that the ultrasonic pulse echo, reflected at reflecting elements in the body, returns back along the same path. The power reflection index or coefficient Ref at the depth z is also frequency dependent and is given empirically by $$\text{Ref} = k(z) \cdot f^{n(z)} \tag{3}$$

k(z) and n(z) are parameters peculiar to the organs of interest at z, and usually n(z) takes a value of 2–4.

The reflected wave is subject to similar attenuation on returning to the body surface where it is received again by the transducer 35 and converted to an electrical signal. The arrival time t of the returning echo reflected at the depth z is given as $t = 2z/C$, where C is the ultrasonic sound propagation speed in the object. The time origin $t = 0$ is taken when a pulse is incident on the body surface $z = 0$. Assuming that the sound speed in the object is constant, the depth z is proportional to the time t of returning, so that it is possible to choose the echo signal from the depth of the desired point by applying a time gate of width $T_g$ which has enough time length to cover the pulse length. This gated signal is obtained by reading out the train of the A/D converted and stored echo signal data of time width $T_g$ corresponding to the time t (depth z) from the memory of the computer. The width of $T_g$ is desirable to be equal to the pulse width ($2 \times T_{\frac{1}{2}}$) or longer. The received signal thus read out will be referred to as the echo pulse in the following.

One of the acoustic characteristics of human tissue that is useful to measure and display as a tomographic image is the attenuation slope given in (2) as a function of z. The principle for obtaining this characteristic will now be described.

Assuming that the originally incident ultrasonic pressure wave incident the tissue has a Gaussian waveform, then its power spectrum also has a Gaussian form as expressed in the following equation, $$|P(f)|^2 = Ae^{-\frac{(f-f_0)^2}{2\sigma^2}} \tag{4}$$

where, $|P(f)|^2$ is the power spectrum of the originally incident ultrasonic pulse pressure wave, and $\sigma^2$ is the variance of the Gaussian distribution. Then, the power spectrum of the echo pulse is given in the following formula, $$|Pe(f)|^2 = A \cdot K \cdot e^{\frac{B(B\sigma^2 - 2f_0)^2}{2}} \cdot e^{-\frac{\{(f-(f_0-\sigma^2 B)\}^2}{2\sigma^2}} \cdot f^n \tag{5}$$

where, $|Pe(f)|^2$ is the power spectrum of the echo pulse, A and K are constants independent of the frequency, and B is given by $$B = 4 \int_0^z B(z)dz$$

As known from equation (5), when n is equal to 0, that is, when the power reflection index is independent of the frequency, the power spectrum of the echo pulse has a Gaussian distribution and the variance remains unchanged, but its center frequency $f_{z0}$ is shifted downwards. This down-shift of the center frequency is expressed as;

$$f_0 - f_{z0} = \sigma^2 \cdot B \tag{6}$$
$$= 4\sigma^2 \int_0^z B(z) \cdot dz$$

The center frequency $f_0$ is known and $f_{z0}$ can be obtained for each fixed value of z by processing the spectra of the echo pulses with the computer 39. Hence, the attenuation slope distribution can be obtained as a function of z by differentiation or by taking the difference of the obtained ($f_0 - f_{z0}$) for various values of z.

In the same way, the attenuation slope distribution $\beta(z)$ can be obtained along other scan lines shifted in parallel to the z axis, for covering the portion of interest of the object (B-mode image). Thus two or three dimensional imaging of the object is provided and displayed on an imaging screen such as a CRT screen. This imaging of the attenuation slope is utilized for diagnosis of cancer and the like by comparing it with that of a normal organ. These devices are a powerful and effective means for various medical uses.

The above-described devices are representative of conventional ones utilizing the power spectrum profile of a propagating wave such as ultrasonic sound. But there remains still two problems with these prior art devices in current use. One problem is that n in the equation (3) is not 0, which means that the reflection indices are variable depending on the frequency, but this can be solved as will be described later. Another problem is the scalloping which appears in the recovered power spectrum profile as described above. One of the objects of the present invention is to provide a means to solve this problem.

Figure 5:
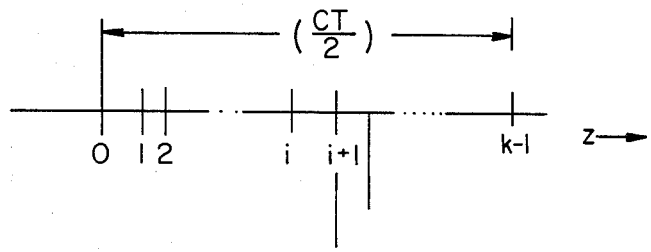
FIG. 5 illustrates schematically the location of reflecting elements inside the object.

The physical principle will be described first. As depicted in FIG. 5, it is assumed that k reflecting elements exist along the z axis within the region of CT/2, where C is the ultrasonic sound speed in the medium and T is the pulse length. A reflected ultrasonic pressure wave at the edge of the region, z=0, is denoted by $r_0 P_{e0}(t)$, and the one at the ith reflecting element is denoted by $r_i P_{ei}(t)$. Both wave shapes are kept the same as expressed by $$r_i P_{ei}(t) = r_i P_{e0}\left(t - \frac{2z_{0i}}{C}\right) \tag{7}$$

where $z_{0i}$ is the distance between the reflecting elements 0 and i, and $r_i$ is the acoustic pressure reflection coefficient, which is positive or negative and usually is below 10% in biological tissue.

Consider the composite wave $P_{s2}(t)$ of two echo pulses from i=0 and i=1, $$\left.\begin{array}{l} P_{s2}(t) = r_0 P_{e0}(t) + r_i P_{e0}\left(t - \frac{2z_{0i}}{C}\right) \\ |P_{s2}|^2 = |P_e(f)|^2 \cdot |SF_2|^2 \\ \text{where,} \\ |SF_2|^2 = r_0^2 + r_1^2 + 2r_0 r_1 \cos 2\pi \left(\frac{2z_{0i}}{C}\right) \cdot f \\ |Pe(f)|^2 = \text{power spectrum of } P_{e0}(t) \end{array}\right\} \tag{8}$$

The overlapped wave of k echo pulses denoted by i=0, i=1, ... i=k−1 is given by $$P_{sk}(t) = \sum_{i=0}^{k-1} r_i P_{e0}\left(t - \frac{2z_{0i}}{C}\right) \tag{9}$$

$$|P_{sk}|^2 = |P_{e0}(f)|^2 \cdot |SF_k|^2$$

$$|SF_k|^2 = \sum_{i=0}^{k-1} r_i^2 + \sum_{i=0}^{k-1} \sum_{q=i+1}^{k-1} 2r_i r_q \cos 2\pi \left(\frac{2z_{iq}}{C}\right) \cdot f$$

The distance between adjacent reflecting elements provides the smallest $z_{iq}$ and actually is around 10 μm for cells in tissue of the human body, and the largest one is ±CT/2 as described above (T=pulse length). The minus sign expresses the distance from a preceding echo and the pulse sign the distance from a delaying echo.

Taking the logarithm of the equation (9) to obtain the cepstrum, $$\ln|P_{sk}|^2 = \ln|P_{e0}(f)|^2 + \ln R_0^2 + \tag{10}$$

$$\ln\left(1 + \sum_{i=0}^{k-1} \sum_{q=i+1}^{k-1} \frac{2r_i r_q}{R_0^2} \cos 2\pi \frac{2z_{iq}}{C} \cdot f\right)$$

where $$R_0^2 = \sum_{i=0}^{k-1} r_i^2$$

Considering that $|r_i r_q|/R_0^2$ is small in comparison to 1, and using the approximation formula, $$\ln(1+x) = x \qquad x \ll 1$$

the equation (10) can be approximated by $$\ln|P_{sk}|^2 = \ln|P_{co}(f)|^2 + \ln R_0^2 + \sum_{i=0}^{k-1} \sum_{q=i+1}^{k-1} \frac{2r_i r_q}{R_0^2} \cos 2\pi \frac{2z_{iq}}{C} \cdot f \qquad (11)$$

The second term is independent of the frequency and the third term corresponds to scalloping. The cepstrum is obtained by performing the Fourier transformation of (11).

As can be seen, the third term of equation (11) has line spectra at the quefrency $\tau_{iq}$, where $$\tau_{iq} = 2z_{iq}/C$$

and the respective magnitude is $2r_i r_q/R_0^2$ (a positive or negative real number) and has no imaginary part.

The magnitude of the cepstrum of the first term of the equation (11) is obtained as follows. Considering the equation (5), $$|P_{co}(f)|^2 = A' \cdot e^{-\frac{(f-f_{z0})^2}{2\sigma^2}} \cdot f^n \qquad (12)$$

where $$A'(z) = A \cdot K \cdot \exp\{\tfrac{1}{2} \cdot B(B\sigma^2 - 2f_0)\}$$

$$B(z) = 4 \int_0^z B(z) dz$$

$$f_{z0} = f_0 - \sigma^2 B$$

Therefore $$\ln|P_{co}(f)|^2 = \ln A'(z) - \frac{(f - f_{z0})^2}{2\sigma^2} + \ln f^n \qquad (13)$$

The cepstrum of the first term of equation (11) is obtained by performing Fourier transformation of equation (13) where the first term is independent of frequency f, and the second and third terms are not periodic functions extending to infinity. Accordingly, their transformation is performed numerically by limiting the dynamic range (ordinate) within 40–60 db.

Figure 6A:
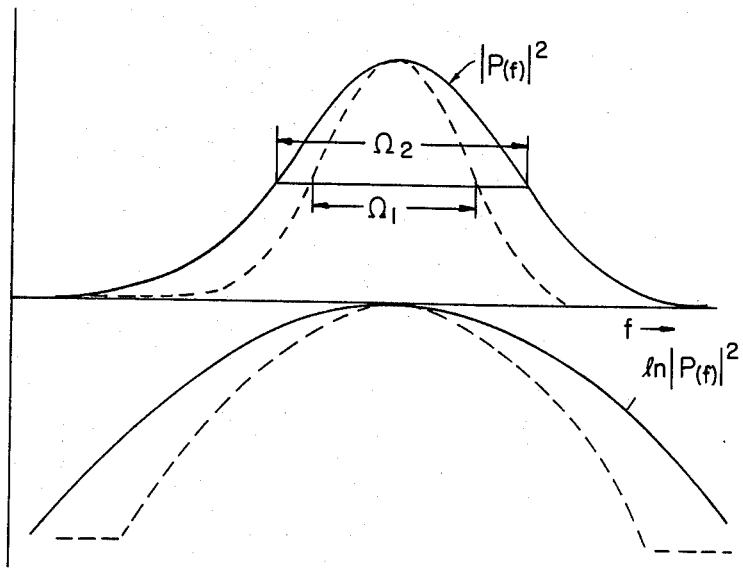
FIG. 6(a) illustrates two examples of power spectrum profiles and their corresponding logarithms.
Figure 6B:
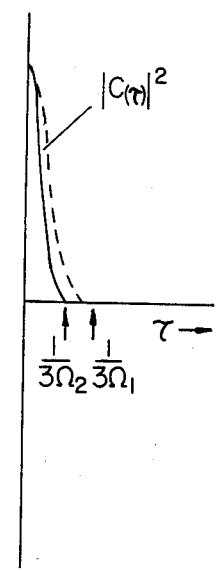
FIG. 6(b) illustrates the power cepstra of the power spectra shown in FIG. 6(a)

The second term of equation (13) corresponds to the travelled power spectrum $|P(f)|^2$ shown in FIG. 6($a$) having a Gaussian shape, and its logarithm curve (a parabola) is shown in the lower part of FIG. 6($a$). The solid line is for the power spectrum having a fractional bandwidth $\Omega_2/f_{ZO}$ OF 71% and the dotted line is for the case of 47%. As can be seen in the figure, the logarithm curve with the dotted line has a horizontal (constant) portion at both its ends, which are the lower power spectra limited to be constant. The power cepstrum $|C(\tau)|^2$ of the second term of equation (13) is depicted in FIG. 6($b$), most of which exists at the quefrency region smaller than $\tfrac{1}{3}\Omega$. It is easily proved that the non-zero magnitude of the cepstrum obtains in the quefrency range below $\tfrac{1}{2}\Omega$.

Figure 7A:
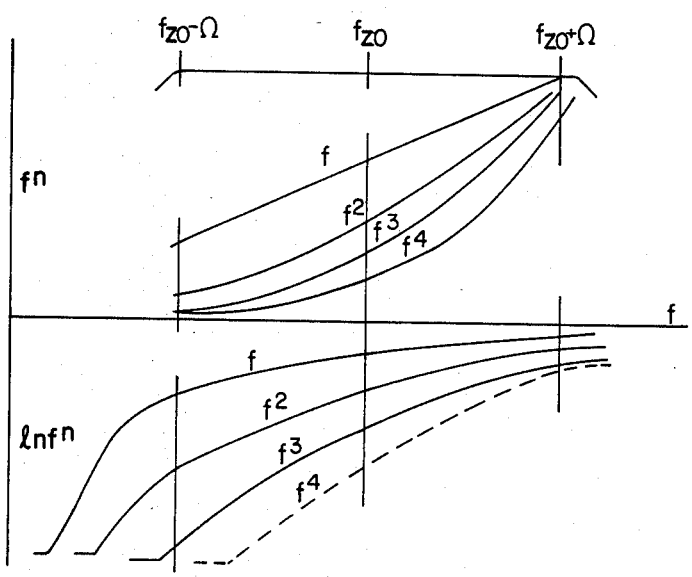
FIG. 7(a) illustrates curves of $f^n$ for several values of the parameter n (above) and their logarithms (below)
Figure 7B:
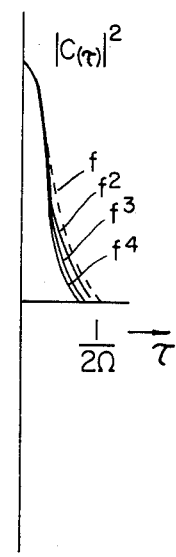
FIG. 7(b) illustrates the cepstra of $f^n$ for several values of the parameter n.

The Fourier transformation of the third term, $\ln f^n$, is performed by multiplying the $f^n$ curve with a window that is flat in the frequency region of $f_{z0} \pm \Omega$ and decreases sinusoidaly. Results are illustrated in FIG. 7($a$) and ($b$). The functions and their logarithm curves are shown in FIG. 7($a$) for several values of the parameter n, and the power cepstra are shown in FIG. 7($b$). The cepstra also exist only in the region of quefrency below $\tfrac{1}{2}\Omega$.

Summarizing the above results, the magnitude cepstrum diagram of the whole power spectrum of the received ultrasonic pressure wave according to equation (13) is obtained and illustrated in FIG. 8($a$). The cepstrum is a smooth curve originated from a Gaussian distribution and a frequency dependent $f^n$ effect and is superposed with line cepstra. Accordingly, this cepstrum curve in FIG. 8($a$) is processed to first eliminate the line or line-like cepstra, while the $f^n$ and incident Gaussian components remain.

There are four methods to achieve this purpose.

First Method: If a Fourier transformation is performed again with the cepstrum curve of FIG. 8($a$), the spectrum of the cepstrum corresponding to the Gaussian distribution and the $f^n$ effect occurs in a lower neo-frequency region, and the components corresponding to line cepstra exist in a considerably higher neo-quefrency region. Accordingly, a linear lowpass filtering of the cepstrum, which functions to cut the spectra existing in the higher neo-frequency, provides a smooth curve as in FIG. 8($b$). Essentially, this method works well if the cepstrum curve of FIG. 8($a$) contains line spectra whose plus and minus values and their respective occurring frequencies are approximately balanced as illustrated in the curve shown in FIG. 8($c$). In this case, the low frequency components due to the line cepstra that still remain after filtering will be minute.

But, generally, when the line or line-like cepstra in the curve of FIG. 8($a$) are spaced closely and overlap to some extent, there appears lower neo-frequency components, which distort the recovered power spectrum. Accordingly, the reforming or correction of the spectrum to a Gaussian shape is still necessary and its method will be described later.

Second Method: This is a method utilizing a non-linear filter. The line-like cepstra of the curve of FIG. 8($a$) are eliminated with a non-linear filter such as a median-filter. This method is suitable when the curve of FIG. 8($a$) has line-like cepstra superposed sparsely on a slowly varying cepstrum. This method is suitable when the curve of FIG. 8($a$) has line-like cepstra superposed sparsely on a slowly varying cepstrum. This method is also effective to reduce the lower neo-frequency components remaining after filtering the line-like cepstra when the line-like cepstra have a dominant positive portion rather than a negative portion like a power cepstrum.

Third Method: This is a method combining the first method or the second method described above with the method of cutting off all the cepstrum of the curve of FIG. 8($a$) corresponding to the higher quefrency region above $\tfrac{1}{2}\Omega$ where the smooth curve of FIG. 8($b$) does not extend. This is effective to increase the merit of the first or second method.

Fourth Method: For the first step of the fourth method, like in the third method, the cepstrum curve corresponding to higher quefrency above $\tfrac{1}{2}\Omega$ is cut off without any filtering as in the first rf second methods. The line-like cepstra in the lower quefrency range below $\tfrac{1}{2}\Omega$ still remain and cause distortion of the power spectrum when inversely transformed. This distortion can be corrected and eliminated using the distortion indices as examined hereafter.

Now, the method to eliminate the distortion of the power spectrum obtained from the processed cepstrum according to the third or fourth method will be described. This method is also applicable to the power spectrum obtained with other methods.

With the fourth method, the residual line cepstra appear as slow scallopings in the power spectrum recovered by inverse transformation, whose shape is expressed by equation (9), by eliminating terms corresponding to the scallopings of higher quefrency as follows $$|SFk|^2 = R_0^2 \left\{ 1 + \sum_{l,m} \frac{2r_l \cdot r_m}{R_0^2} \cos 2\pi \left( \frac{2z_{lm}}{C} \right) f \right\} \quad (14)$$

where $$\frac{2z_{lm}}{C} \leq \frac{1}{2\Omega}$$

The most rapidly varying scalloping appears when $z_{lm}$ is given by the equation $$\frac{2z_{lm}}{C} = \frac{1}{2\Omega}.$$

The most rapid scalloping, for $\Omega = 0.47 f_{z0}$ and $\Omega = 0.71 f_{z0}$, is illustrated in FIG. 9, having more slowly varying curves than the curve of the travelled power spectrum $|P_{z0}(f)|^2$. The line cepstra corresponding to the quefrency lower than $\frac{1}{2}\Omega$ will naturally have further slower scalloping. Therefore, the equation (4) can be expanded with satisfactory approximation as $$|SFk|^2 = S\{1 + p'(f-f_{z0}) + q'(f-f_{z0})^2\} \quad (15)$$

wherein $p'$ and $q'$ are Taylor's expansion coefficients of first and second order terms and the third and higher order terms are neglected.

The residual part of the cepstra, derived from $f^n$ in the lower quefrency region, are inverse-transformed and become again $f^n$ functions which show also slowly varying curves. Accordingly, they can be expanded in the range of $f_{z0} \pm \Omega$ and approximated as follows:

$$f^n = f_{z0}^n \{1 + p''(f-f_{z0}) + q''(f-f_{z0})^2\} \quad (16)$$

Utilizing approximated results as given in equations (15), (16), the final approximated expression of the power spectrum of the received signal is obtained from the equation (9) as follows;

$$|P_{sk}|^2 = A_0 e^{-\frac{(f-f_{z0})^2}{2\sigma^2}} \cdot \{1 + p(f-f_{z0}) + q(f-f_{z0})^2\} \quad (17)$$

where $$A = A' \cdot f_{z0}^n \cdot S$$

and p, q are distortion indices that are functions of $p'$, $q'$, $p''$ and $q''$.

An ultrasonic pressure wave with a Gaussian spectrum should keep its profile as the wave travels through a medium as described above, so that a received signal should have also a Gaussian spectrum with the same variance. Actually, it is subject to some distortion. The indices p and q provide this distortion, and are obtained from the actual spectrum of the received signal by measuring the deviation from an exact Gaussian spectrum.

Thus it is possible to correct and recover the original Gaussian spectrum with the resulting p and q.

Next, the method of determining p and q will be described.

One of the methods is a moment method. At first, moments of several orders are calculated, such as $$M_0 = \int_{-\infty}^{+\infty} |Psk|^2 df$$

$$M_1 = \int_{-\infty}^{+\infty} f|Psk|^2 df$$

The center frequency $f_a$ of the distorted distribution is given through $$\frac{M_1}{M_0} = f_{z0} + \frac{p\sigma^2}{1 + q\sigma^2} = f_a \quad (18)$$

The second and third moments around $f_a$ are given by $$M_2 = \int_{-\infty}^{+\infty} (f-f_a)^2 |Psk|^2 df$$

$$M_3 = \int_{-\infty}^{+\infty} (f-f_a)^3 |Psk|^2 df$$

$M_0$, $M_1$, $M_2$, $M_3$ and $\delta$ are obtained for the measured spectrum, then p and q can be calculated by the following equations.

$$\frac{M_2}{M_0} = \sigma^2 - \frac{p^2 \sigma^4}{(1 + q\sigma^2)^2} + \frac{2q\sigma^4}{1 + q\sigma^2} \quad (19)$$

$$\frac{M_3}{M_0} = 2 \left( \frac{p}{1 + q\sigma^2} \right)^3 \cdot \sigma^6 \left( 1 - \frac{3q(1 + q\sigma^2)}{p^2} \right) \quad (20)$$

Assuming that $q=0$, then the formula are simplified, and $f_{z0}$ is given by $$f_{z0} = \frac{M_1}{M_0} - \left( \sigma^2 - \frac{M_3}{2M_0} \right) \frac{1}{3} \quad (21)$$

or $$f_{z0} = \frac{M_1}{M_0} \left( \sigma^2 - \frac{M_2}{M_0} \right) \frac{1}{2} \quad (22)$$

Both equations are available.

Other approximate expressions for the distortion such as $|SF|^2$ and $f^n$ and correcting formula are of course available under this invention.

As described above, the down-shift of the center frequency $f_{z0}$ thus obtained leads to providing the attenuation slope distribution $\beta(z)$ as a function of z. The two or three dimensional imaging is obtained by processing a set of the attenuation slope distributions along a set of scan lines in the region of interest inside the object.

Now another preferred embodiment of the device according to the present invention will be described in connection with FIG. 10. The apparatus is basically the same one illustrated in FIG. 3, except for the signal processing and computing devices.

The A/D converter 108 in FIG. 10 (38 in FIG. 3) outputs a train of A/C converted digital data of the received echo signal. The digital signal is Fourier-transformed with a conventional digital fast Fourier transformer (DFFT) 110 to provide the output power spectrum $|P_e(f)|^2$ the logarithm of which is obtained with a log converter 111. Such a conversion is made by reading a conversion table stored in the read only memory (ROM). The output of the log converter 111, namely $\log |P_e(f)|^2$ is again Fourier transformed with the DFFT 112 and its output provides the cepstrum $C(\tau)$. The $C(\tau)$ is windowed by a lifter 113, thus the cepstra locating in a higher quefrency than $\frac{1}{2}\Omega$ goes to 0. The lifted cepstrum is processed with digital fast inverse-Fourier transformer (DFIFT) 114 to $\ln|P_e(f)|^2$, which is again converted inversely with an antilogarithm converting table in an exponential converting circuit EXP 115. The output derived is the power spectrum $|P_e'(f)|^2$ after homomorphic filtering, and is a distorted Gaussian spectrum containing slow scalloping and a frequency dependency of the reflection index.

The operation units 116, 117, 118, 119 and 120 calculate the following formulas:

$$M_0 = \int |P_e'(f)|^2 df$$
$$M_1 = \int f|P_e'(f)|^2 df \tag{23}$$

$$f_a = M_1/M_0 \tag{24}$$

$$\left.\begin{array}{l} M_2 = \int (f - f_a)^2 \cdot |P_e'(f)|^2 df \\ M_3 = \int (f - f_a)^3 |P_e'(f)|^2 df \end{array}\right\} \tag{25}$$

The operation units are composed of conventional calculators such as adders, multipliers, subtractors and dividers. $M_1/M_0$, $M_2/M_0$ and $M_3/M_0$ are calculated with dividers 120.

With a correction calculator 121, $f_{z0}$ is calculated from equations (18), (19), (20) or one of (21) and (22) for $f_a$. The correction from the higher order approximation, namely equations (18), (19), (20), can be done using a table prepared to provide $f_a - f_{z0}$ as given in equation (18), as a function of $M_2/M_0$, $M_3/M_0$ as given in equations (19), (20). Such a table can be prepared by calculating $f_a - f_{z0}$, $M_2/M_0$, $M_3/M_0$ for possible combinations of $\sigma$, p, q and rearranging the calculated results. Then $f_{z0}$ is obtained from the subtraction $f_{z0} = f_a - (f_a - f_{z0})$.

So the output of the correcting calculator 121 provides a corrected center frequency $f_{z0}$. A differentiator 122 composed of a temporary storage register and a subtractor provides $\beta(z)$ by calculating the difference of $f_{z0}$ at adjacent depths z and $z + \Delta z$ which are outputs from the correction calculator 121 in a time sequential manner.

As a display device, a cathode ray tube 123 is used. Its brightness is modulated with $\beta(z)$ and the spot position is controlled in a similar manner to correspond to the actual depth z and the scan line location (X-coordinate). The attenuation slope distribution over a tomographic X-Z plane of the object is imaged on the screen surface of the tube.

With an apparatus as illustrated in FIG. 10, the operation of each component is controlled by a clock circuit 101 (the controlled points are denoted with arrows accompanied by a letter C) and operates within every period T of the time gate length, and the output of every stage is trasmitted to the subsequent stage, so that the apparatus is structured as a pipeline-processor for real-time processing. However, when the processing speed of the components are not fast enough for the imaging process, a buffer memory 124 is added after the EXP 115 for storing the signal temporarily, and the signal is processed later so as to match the operating speed of each stage, that is, on a non-real time basis.

Furthermore, the distribution of the other acoustic characteristics, such as the reflection index, acoustic impedance and the like, of the object can be derived utilizing the obtained $\beta(z)$. The distribution of the 0th moment of the power spectrum processed by this invention provides a speckle-less B-mode image. Moreover, other characteristics can be obtained more exactly.

The above embodiments were described regarding an ultrasonic apparatus for medical use, but the present invention is applicable to radar, sonar, surveying of geologic structure, transmission ultrasonic CT, and the like.

In the above described explanation, it has been assumed that the originally incident ultrasonic pressure wave or its power spectrum has a Gaussian profile. A description will now be given for a non-Gaussian profile of the originally incident pulse.

Contrary to the equation (4) in the former case, the non-Gaussian profile can be approximated by the following equation which is similar to equation (17).

$$|P(f)|^2 = A \cdot e^{-\frac{(f-f_0)^2}{2\sigma^2}} \cdot (1 + p_0(f - f_0) + q_0(f - f_0)^2) \tag{26}$$

The parameters in the equation (26), $f_0$, $\sigma^2$, $p_0$ and $q_0$, are determined as follows from the measured spectrum.

With the measured spectrum, moment ratios of $M_1/M_0$, $M_2/M_0$, $M_3/M_0$, maximum spectrum frequency $f_m$ or half-maximum-width $\Omega_a$ are obtained, and substituted into the equations (18), (19), (20), and one of the following equations is derived from (26):

$$p_0 + (2q_0 - 1/\sigma^2)(f_m - f_0) - p_0/\sigma^2(f_m - f_0)^2 - q_0/\sigma^2(f_m - f_0)^3 = 0 \tag{27}$$

$$(q_0 - \tfrac{1}{2}\sigma^2)^2 \Omega_a{}^2 = p_0 - 4(\ln \tfrac{1}{2}) \cdot (q_0 - \tfrac{1}{2}\sigma^2) \tag{28}$$

Then $p_0$, $q_0$, $\sigma^2$, $f_0$ are obtained by solving the four equations. Thus the spectrum profile of the originally incident pulse wave is approximated with the equation (26).

The echo pulse spectrum is given by the following equations.

$$|P_e(f)|^2 = A \cdot e^{-\frac{(f-f_0)^2}{2\sigma^2}} \cdot \{1 + p_0(f - f_0) + q(f - f_0)^2\} \cdot e^{-Bf} \cdot K \cdot f^n \tag{29}$$

When $n = 0$, the spectrum of the echo pulse is expressed by:

$$|P_e(f)|^2 = A_z \cdot e^{-\frac{(f-f_{z0})^2}{2\sigma^2}} \cdot \{1 + p_z(f - f_{z0}) + q_z(f - f_{z0})^2\} \tag{30}$$

wherein $$A_z = A \cdot K \cdot (1 + p_0 f_{z0} + q_0 f_{z0}^2) \cdot e^{\sigma^2 B(2\sigma^2 - 2f_0)}$$

$$P_z = \frac{p_0 + 2q_0 f_{z0}}{1 + p_0 f_{z0} + q_0 f_{z0}^2}, \quad q_z = \frac{q_0}{1 + p_0 f_{z0} + q_0 f_{z0}^2} \tag{31}$$

-continued $$f_{z0} = f_0 - \sigma^2 B$$

$$B = 4 \int_0^z \beta(z)\, dz$$

Accordingly, the spectrum of the echo pulse (31) has a similar form to that of the originally incident pulse (26) but with a frequency down-shift $f - f_{z0}$. The variance $\sigma^2$ remains unchanged and $f_{z0}$, $p_z$ and $q_z$ are obtained by the equations (18), (19), (20) and (30). The frequency down-shift is given through equation (31), $$f_0 - f_{z0} = 4\sigma^2 \int_0^z \beta(z)\, dz$$

and the attenuation slope distribution $\beta(z)$ is obtained by taking the frequency down-shift for various sequential values of z.

When n is not equal to 0, the slowly varying scalloping and $f^n$ factors remain after homomorphic filtering, the spectrum given by the equation (17) is combined with the equation (29), and an equation similar to equation (30) is obtained, but with $p_z$ and $q_z$ replaced by $p_z'$ and $q_z'$, respectively. As the form of the equation remains the same, the factors $f_{z0}$, $p_z'$ and $q_z'$ can be obtained.

In the above embodiments, the way of obtaining an attenuation slope utilizing the center frequency down-shift were described. But other characteristics, utilizing the spectrum profile itself, corrected with the $p_0$, $q_0$; $p_z$, $q_z$; $p_z'$, $q_z'$ are available for either a Gaussian or a non-Gaussian spectrum.

A lowpass filtered and/or liftered cepstrum was used for removing rapid scalloping in the above description, but a highpass filtered cepstrum is available to obtain line or line-like cepstra as shown in FIG. 8(c). In this figure the abscissa represents the distance between every combination of reflecting elements within the pulse length positioning at the depth z and the ordinate represents the sum of reflection intensity products of every reflecting point pair having the same separation. Therefore, the micro-structure of a heterogeneous medium such as biological tissue can be estimated with the highpass filtered or liftered cepstrum.

This patent utilizes the processing means in the cepstrum domain to remove scalloping and the correction means by the distortion indices of the processed spectrum. However, the cepstrum processing can be replaced by any other method for effectively reducing the effect of scalloping. For example, conventional statistical averaging for reducing the effect of scalloping can be incorporated in the correction means according to the distortion indices of the statistically processed spectrum. This is within the scope of the present invention.

For example, by calculating the spectrum momenta of 0th order and first order, the mean size of the microstructure of a tissue can be estimated, as mean quefrency, which provides a parameter representing another tissue characteristic and will contribute to the medical diagnosis.

What is claimed is:

1. An apparatus utilizing the profile of a travelled power spectrum of a received signal wave of pulses transmitted through or reflected in an object, corresponding to an originally incident pulse having a predetermined power spectrum, to measure the characteristics of said object, said apparatus comprising:
   processing means for reducing the scalloping of the travelled power spectrum of said received signal wave;
   recovery means for deriving the travelled power spectrum with the reduced scalloping; and
   extracting means for extracting information on the characteristics of said object from the derived power spectrum.

2. The apparatus of claim 1, wherein said processing means includes:
   means for deriving a cepstrum of said received signal wave;
   filtering means for separating line-like rapidly varying components of said cepstrum from slowly varying components of said cepstrum; and
   inverse transformation means for deriving a power spectrum for said filtered cepstrum.

3. The apparatus of claim 1, wherein said processing means includes means for deriving a cepstrum of said received signal wave, a highpass filter for rejecting slowly varying cepstrum components and for passing line-like rapidly varying cepstrum components.

4. The apparatus of claim 3, wherein said filtering means comprises a non-linear lowpass filter for rejecting the line-like rapidly varying cepstrum components.

5. The apparatus of claim 1, wherein said recovery means comprises means for obtaining distortion indices of said derived power spectrum after liftering and for correcting the respective distortion of said derived power spectrum after liftering based on said indices.

6. An apparatus according to claim 5, said filtering means comprising means for setting a cutoff quefrency $\tau_c$ within plus and minus 50% of the reciprocal of twice the band-width of the spectrum of said originally incident pulse.

7. An apparatus according to claim 1, comprising means for providing said originally incident pulse with one of a Gaussian and quasi-Gaussian shaped power spectrum.

8. An apparatus according to claim 1, further comprising:
   means for transmitting said originally incident pulse with a non-Gaussian power spectrum;
   means for approximating the received signal corresponding to said non-Gaussian spectrum with a product of a Gaussian distribution and a polynomial of the nth power of frequency; and
   means for processing said Gaussian distribution as if it were the whole spectrum of said originally incident pulse.

9. An apparatus according to claim 1, wherein said derived power spectrum has a distortion, and said recovery means further comprises means for estimating respective distortion indices of said derived power spectrum and for estimating the center frequency of a respective undistorted Gaussian spectrum, from said derived power spectrum with the aid of said distortion indices.

10. An apparatus according to claim 1, wherein said recovery means further comprises:
    means for calculating a plurality of monments of respective orders from said derived power spectrum; and
    means for calculating distortion indices of said derived spectrum using said moments.

11. An apparatus according to claim 1, wherein said moments include the moments $M_0$, $M_1$, $M_2$ and $M_3$ of zeroth, first, second and third order, respectively, said derived power spectrum is distorted, and said recovery means comprises means for correcting the distortion of said derived power spectrum by providing a correction from the following equations $$\frac{M_1}{M_0} = f_{z0} + \frac{p\sigma^2}{1 + q\sigma^2} = f_a$$

$$\frac{M_2}{M_0} = \sigma^2 - \frac{p^2\sigma^4}{(1 + q\sigma^2)^2} + \frac{2q\sigma^4}{1 + q\sigma^2}$$

$$\frac{M_3}{M_0} = 2\left(\frac{p}{1 + q\sigma^2}\right)^3 \cdot \sigma^6\left(1 - \frac{3q(1 + q\sigma^2)}{p^2}\right)$$

using a table prepared to provide $f_a - f_{z0}$ according to the first equation above as a function of $M_2/M_0$ and $M_3/M_0$ as given by the second and third equations above, respectively, said table being prepared by the calculation of $f_a - f_{z0}$, $M_2/M_0$, $M_3/M_0$ for respective combinations of p, q and associated calculated results, and by performing the subtraction $f_{z0} = f_a - (f_a - f_{z0})$ to obtain $f_{z0}$, where $f_a$ is the center frequency of the distorted spectrum, $f_{z0}$ is the downshift of the center frequency of the distorted spectrum, $\sigma$ is the variance of the Gaussian component of the originally incident power spectrum, and p and q are distortion indices.

12. An apparatus according to claim 1, further comprising:
  means for providing said signal wave;
  imaging means for imaging a characteristic of a biological tissue in said object; and
  display means for displaying an image of said characteristic with a B mode image.

13. The apparatus of claim 12, said characteristic being selected from an attenuation coefficient, a reflection coefficient and a measure of heterogeneity.

14. The apparatus of claim 10, said distortion indices being selected from the center frequency, the bandwidth, the skew, and correction factors of said derived power spectrum.

* * * * *

UNITED STATES PATENT AND TRADEMARK OFFICE
CERTIFICATE OF CORRECTION

PATENT NO. : 4,545,250
DATED : October 8, 1985
INVENTOR(S) : Hirohide Miwa

It is certified that error appears in the above-identified patent and that said Letters Patent is hereby corrected as shown below:

Column 3, line 33, "fctors" should be --factors--.

Column 6, line 45 "2-4" should be --2~4--.

Column 7, line 41-42, delete "∫" st the margin.

Column 8, line 30 "$(20z_{oi}/C)$" should be --$(20z_{ol}/C)$--.

Column 16, line 64, "monments" should be --moments--.

Signed and Sealed this

Fourth Day of February 1986

[SEAL]

Attest:

DONALD J. QUIGG

Attesting Officer     Commissioner of Patents and Trademarks